(12) United States Patent
Guo

(10) Patent No.: US 12,167,955 B2
(45) Date of Patent: Dec. 17, 2024

(54) SURGICAL PROSTHETIC

(71) Applicant: Davol Inc., Warwick, RI (US)

(72) Inventor: Joshua Yao Guo, Providence, RI (US)

(73) Assignee: Davol Inc., Warwick, RI (US)

( * ) Notice: Subject to any disclaimer, the term of this patent is extended or adjusted under 35 U.S.C. 154(b) by 869 days.

(21) Appl. No.: 17/275,817

(22) PCT Filed: Oct. 3, 2019

(86) PCT No.: PCT/US2019/054439
§ 371 (c)(1),
(2) Date: Mar. 12, 2021

(87) PCT Pub. No.: WO2020/072742
PCT Pub. Date: Apr. 9, 2020

(65) Prior Publication Data
US 2022/0047369 A1 Feb. 17, 2022

Related U.S. Application Data

(60) Provisional application No. 62/741,180, filed on Oct. 4, 2018.

(51) Int. Cl.
*A61F 2/00* (2006.01)
(52) U.S. Cl.
CPC .... *A61F 2/0063* (2013.01); *A61F 2220/0016* (2013.01); *A61F 2220/0075* (2013.01)
(58) Field of Classification Search
CPC ............ A61F 2/0063; A61F 2220/0016; A61F 2/0045; A61F 2220/0075;
(Continued)

(56) References Cited

U.S. PATENT DOCUMENTS 8,308,758 B2    11/2012  Åkerfeldt
2002/0123750 A1*  9/2002  Eisermann ............. A61B 17/68
                                          606/76
(Continued)

FOREIGN PATENT DOCUMENTS

WO    WO-2007097994 A2 *  8/2007  ......... A61B 17/0401
WO    WO 2009/017680 A2   2/2009
WO    WO 2010/028242 A1   3/2010

OTHER PUBLICATIONS

International Search Report and Written Opinion for International Application No. PCT/US2019/054439, mailed Dec. 18, 2019.
(Continued)

*Primary Examiner* — Katherine M Shi
(74) *Attorney, Agent, or Firm* — Wolf, Greenfield & Sacks, P.C.

(57) ABSTRACT

Embodiments disclosed herein relate to prosthetics for augmenting or repairing a tissue defect, such as a ventral or incisional hernia. In some embodiments, a repair prosthetic may include a patch body and a first fastener attached to a first portion of the patch body. A coupler may be attached to and extend from a second portion of the patch body, and a second fastener may be attached to the second portion of the patch body via the coupler. The coupler may be retracted relative to the second portion of the patch body or the second fastener to apply tension to the patch body in some embodiments.

20 Claims, 6 Drawing Sheets

(58) Field of Classification Search
CPC ....... A61F 2002/3055; A61B 2017/081; A61B 17/08; A61B 17/085; A61B 2017/086; A61B 2017/088; A61B 17/0466
See application file for complete search history.

(56) References Cited

U.S. PATENT DOCUMENTS

| | | | | |
|---|---|---|---|---|
| 2006/0252980 | A1* | 11/2006 | Arnal | A61B 17/0401 600/151 |
| 2009/0221868 | A1 | 9/2009 | Evans | |
| 2010/0094079 | A1* | 4/2010 | Inman | A61B 17/0401 600/30 |
| 2010/0261955 | A1* | 10/2010 | O'Hern | A61F 2/0063 600/37 |
| 2011/0270284 | A1* | 11/2011 | Beauchamp | A61F 2/0063 606/151 |
| 2011/0288368 | A1* | 11/2011 | VanDeWeghe | A61F 2/0045 600/30 |
| 2014/0257032 | A1* | 9/2014 | Hacker | A61B 17/06109 600/37 |
| 2016/0220252 | A1* | 8/2016 | Belson | A61B 17/08 |
| 2017/0319319 | A1 | 11/2017 | Fischer | |
| 2018/0193011 | A1 | 7/2018 | Keene et al. | |
| 2019/0151065 | A1* | 5/2019 | Rosenblatt | A61B 17/0482 |

OTHER PUBLICATIONS

[No Author Listed] Skin Closure by Zipline® Medical. Publicly available at least as early as Jul. 27, 2018, 1 page.

* cited by examiner

SURGICAL PROSTHETIC

RELATED APPLICATION

This application is a national stage filing under 35 U.S.C. § 371 of International Patent Application Serial No. PCT/US2019/054439, filed Oct. 3, 2019, which claims the benefit under 35 U.S.C. § 119 (e) of U.S. Provisional Application Number No. 62/741,180, filed Oct. 4, 2018, the contents of each of which is incorporated herein by reference in its entirety.

FIELD

Disclosed embodiments are related to surgical prosthetics for augmenting or repairing tissue defects.

BACKGROUND

Many surgical procedures involve placement of a prosthetic such as a mesh to provide support to a region of tissue. For example, surgical procedures often require access into the abdominal cavity, and a laparotomy may be performed to create an incision through the abdominal wall. After the surgical procedure is completed, the incision is closed, typically with sutures, staples, or other fixation devices. The incision site, even after healing, may be weaker than surrounding tissue and can rupture or bulge—known as an incisional hernia. Accordingly, a surgical prosthetic may be applied over a closed laparotomy incision to strengthen the abdominal wall in the area of the incision, prophylactically reducing the likelihood of an incisional hernia. Surgical prosthetics also may be used to augment other types of hernias, such as ventral hernias, or other soft tissue or muscle wall defects.

SUMMARY

In one embodiment, a prosthetic for augmenting or repairing a tissue defect includes a patch body, a first fastener attached to a first portion of the patch body, and a coupler attached to and extending from a second portion of the patch body. A second fastener is attached to the second portion of the patch body via the coupler.

In another embodiment, a method for fixating a prosthetic to tissue includes fixating a first portion of a patch body to the tissue, and fastening a coupler to the tissue. The coupler extends from the second portion of the patch body. The method further includes shortening a length of the coupler extending between the second portion of the patch body and the tissue to tension the patch body In a further embodiment, a prosthetic for augmenting or repairing a tissue defect includes a patch body, a first support attached to a first portion of the patch body, and a first plurality of fasteners attached to the first support. The prosthetic further includes a plurality of couplers attached to and extending from a second portion of the patch body, a second support attached to the second portion of the patch body via the plurality of couplers and a second plurality of fasteners attached to the second support It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
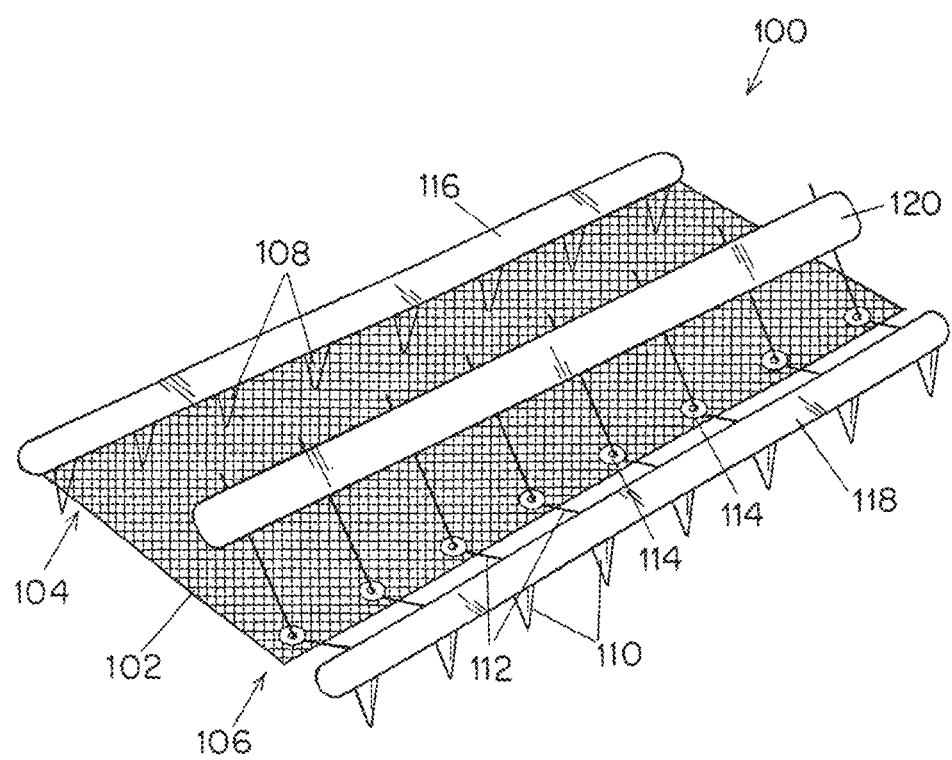
FIG. 1 is a schematic perspective view of a surgical prosthetic, according to one embodiment.

Aspects described herein relate to systems and methods that facilitate placement and fixation of surgical prosthetics for augmenting and/or repairing a tissue defect. The surgical prosthetics described herein include a patch body such as a surgical mesh and may be placed for augmentation, repair and/or prevention of hernias such as ventral hernias or incisional hernias that may form at an incision site in addition to other possible applications. The inventors have recognized and appreciated that conventional approaches for fixating such prosthetics may be subject to variability arising from differences in techniques used by different surgeons. For instance, such variability may lead to an incision site being subjected to tension, which may adversely affect the ability of the tissue to properly heal. Moreover, in some instances, tension on an incision site may necessitate additional surgical steps, such as the creation of relief incisions to relieve tension on the incision site.

In view of the above, the inventors have appreciated numerous advantages associated with surgical prosthetics that can allow for easier placement and fixation of a patch body, and which, in some instances, may allow for substantially tension-free healing of an incision site or other tissue defect. According to some embodiments, the prosthetics and methods described herein may allow for the direct control of tension that is applied to a patch body and the associated tissue when fixating the patch to tissue around an incision site. Such a functionality may help to prevent and/or reduce tension applied to the tissue surrounding an incision or other tissue defect. For example, the prosthetics may allow a surgeon to control the tension applied to a patch body during fixation of the patch body such that the tissue on opposing sides of an incision is substantially tension-free. Additionally, by facilitating easier placement, fixation, and tensioning of a patch body compared to conventional approaches, the prosthetics and methods disclosed herein may provide for reduced variability in patch body tension and/or tension on tissue around an incision or other tissue defect resulting from surgeon technique. This reduction in variability due to surgeon technique may allow for patch bodies to be placed more reliably and more consistently with different surgeons. Moreover, in some embodiments, the prosthetics and methods described herein may aid in maintaining the patch body in a flat and/or conforming configuration against the tissue during both a surgical procedure and/or a subsequent recovery period.

In one embodiment, a prosthetic for augmenting or repairing a tissue defect (e.g., a ventral or incisional hernia) includes at least one first fastener attached to a first portion of a patch body, such as along a first edge of the patch body. One or more couplers extend from a second portion of the patch body (e.g., along a second edge of the patch body which may be opposite the first edge), and one or more second fasteners are attachable to the second portion of the patch body via the coupler(s). In this manner, the coupler(s) may act as a linkage or tether to indirectly attach the second fastener(s) to the second portion of the patch body via the coupler(s). Each of the first and second fasteners may be secured to regions of tissue, such as on opposing sides of a hernia or an incision site, and subsequently, a length of the coupler(s) extending between the second portion of the patch body and the second fastener(s) may be shortened to apply tension to the patch body. As described in more detail below, such shortening of the length of the coupler(s) may be accomplished by retracting the coupler(s) relative to the second portion of the patch body and/or the second fastener(s). Once a desired tension is achieved in the patch body, the coupler(s) may be secured to the second portion of the patch body or the second fastener(s) to fix the patch body in place at the desired tension. As described in more detail below, the coupler(s) may be secured to the patch body or second fasteners in any suitable manner, such as by tying off the coupler(s) and/or via a suitable structure that limits movement of the coupler(s) relative the patch body and/or the second fasteners in one or more directions.

For the sake of clarity, the various embodiments described herein are described in connection with a prosthetic for augmenting and/or repairing a hernia, specifically a ventral or incisional hernia. However, the disclosure is not necessarily so limited, and may be employed in other patch systems for other hernias, other soft tissue or muscle wall defects, as well as may other types of surgical or medical treatments. For instance, as used herein, a tissue defect may refer to a closed incision site, such as a laparotomy incision that is closed via sutures, staples, and or tacks. With respect to repair of a ventral or incisional hernia, the coupler system and patch body may be placed in the intraperitoneal, pre-peritoneal, retromuscular, or other anatomical space, as the disclosure is not so limited. For ease of understanding, the prosthetic is described in connection with an open laparotomy procedure for applying the prosthetic, but the disclosed devices may be employed in other minimally invasive procedures, in an open procedure, or in other techniques for repairing a hernia or other soft tissue defect as the disclosure is not so limited.

A patch body may be formed of any appropriate tissue repair fabric, mesh, or other material. For example, a patch body may be made using a combination of one or more of a porous material, such as a knit fabric, woven or non-woven fabric, and/or a solid, substantially non-porous, or microporous material. The patch body may be formed of one or more layers of the same or dissimilar material, and the layers may be stacked one on top of the other, side-to-side, or include a combination of both stacking arrangements. The patch body may be formed with portions that are tissue infiltratable and other portions that are less tissue infiltratable or are non-tissue infiltratable, providing selected areas of the repair device with different tissue ingrowth and adhesion resistant properties. Further, the patch body may be formed of a permanent material, a resorbable material, or a combination of permanent and resorbable materials. It should also be appreciated that the patch body may be formed of any biologically compatible material, synthetic or natural, suitable for repairing a tissue or muscle wall defect as would be apparent to one of skill in the art.

In view of the above, it should be understood that a patch body may be made from any appropriate material or combination of materials suitable for use in repairing a soft tissue defect, and that the current disclosure is not limited to any particular type of patch body construction.

It should be understood that the prosthetics described herein may include any suitable arrangement of first fasteners to secure the first portion of a patch body to tissue. In some embodiments, the first fasteners may formed as any appropriate surgical fastener construction for attaching the patch body to tissue, including but not limited to, barbed tacks, staples, sutures, adhesive pads, and/or any other appropriate construction. Additionally, the first fasteners may be directly attached to the first portion of the patch body in some embodiments by, for example, passing a least a portion of the first fasteners through the patch body. In other embodiments, the first fasteners may be integrally formed with the patch body and/or with a structure that is attached to the patch body to form a unitary structure. For instance, one or fasteners may be formed in a strip or other structure that is attached to the first portion of the patch body. In another embodiment, the first fastener may comprise an adhesive pad or strip attached to a side of the patch body configured to contact the tissue.

Similar to the above, the prosthetics described herein may employ any suitable arrangement of second fasteners and couplers to secure the second portion of a patch body to tissue, and the couplers may be attached to the second fasteners and the second portion of the patch body in any suitable manner. For example, the second fasteners may be formed as any appropriate surgical fasteners for securing the couplers to tissue including, but not limited to, barbed tacks, staples, sutures, adhesive pads, and/or any other appropriate construction. In some embodiments, each of the second fasteners may include a connector that receives a portion of the coupler to secure the coupler to the fastener. For example, the connector may include a recess or channel constructed and arranged to receive the coupler. In some instances, the coupler may be slidably received in the connector to permit movement of the coupler along at least one direction relative to the second fastener to facilitate retraction of the coupler relative to the second fastening element. In other embodiments, a coupler may be integrally formed with each of the second fastener.

In view of the above, it should be understood that the current disclosure is not limited to any particular type of fasteners for the first and second fasteners, and the prosthetics described herein may employ any suitable fasteners. Moreover, depending on the particular embodiment, the first and second fasteners may generally comprise the same type of fastener, or they may comprise different types of fasteners, as the current disclosure is not limited in this regard.

As noted above, the surgical prosthetics disclosed herein include one or more second fasteners attached to a second portion of the patch body via one or more couplers extending from the second portion of the patch body. It should be understood that the current disclosure is not limited to any particular construction for the couplers. For example, in some embodiments, the couplers may be formed as a length of suture or other similar thread-like material, and in this manner, the couplers may act as tethers that connect the second fasteners to the second portion of the patch body. However, embodiments in which a coupler is a different construction than a suture are also contemplated. For example, a coupler may be embodied as any construction that is capable of being attached to and applying tension to an associated patch body relative to an associated fastener including, for example, strips, rods, films, and/or filaments to name a few. In some embodiments, the couplers may be flexible and/or may impart little to no structural support to a prosthetic when not tensioned, while in other embodiments, a coupler may be formed of a semi-rigid material. Moreover, it should be appreciated that the couplers may be formed of any suitable material as would be apparent to one of skill in the art, including, but not limited to, a permanent material, a resorbable material, a combination of permanent and resorbable materials, a biologically compatible material, a synthetic material, and/or a natural material.

According to some aspects of the current disclosure, one or more coupler(s) may be configured such that that the coupler(s) may only move substantially along one-direction relative to the second portion of the patch body and/or the second fastener(s). For example, in some embodiments, a coupler may comprise a one-way suture (e.g., a suture comprising barbs or other suitable features that are engageable with a corresponding structure attached to the patch body or fastener to limit motion of the suture to substantially along a single direction), a ratcheting arrangement, and/or any other suitable arrangement such that the coupler is limited to move substantially along a single direction to shorten a length of the coupler extending between the second fastener(s) and the corresponding second portion of the patch body. For instance, the coupler(s) may be retractable relative to the second portion of the patch body or the second fasteners to tension the patch body, and such features to limit movement of the couplers along a single direction may limit or prevent loosening of the couplers after tensioning the patch body. In some embodiments, such features may be sufficient to maintain the patch body in a tensioned configuration after retracting the couplers without requiring a surgeon to perform additional steps, such as tying off the couplers. In other embodiments, such arrangements may provisionally secure the patch body in a tensioned configuration while a surgeon ties off the coupler to permanently secure the patch body in a desired tensioned configuration.

In some embodiments, a patch body may include one or more grommets located in the second portion of the patch body and configured to receive the coupler(s). For example, the grommets may provide structural support to aid in avoiding damage to the patch body when the patch body is tensioned from the associated couplers applying force directly to the patch body. Alternatively or additionally, in some embodiments the grommets may interact with features on the couplers to limit movement of the couplers to a single direction through the patch body. For example, the grommets may provide a support against which barbs (or other suitable structures) on a one-way suture may engage to substantially prevent backwards movement of the suture when the coupler is retracted relative the patch body. In other embodiments, a grommet may include a pawl that engages with features on the coupler to form a ratcheting configuration that limits motion of the coupler along one direction relative to the second portion of the patch body. While various arrangements for the grommets are described herein, it should be understood that the current disclosure is not limited to any particular arrangement for the grommets.

Moreover, grommets may not be included in some embodiments (e.g., in embodiments utilizing a patch body comprising a tightly woven mesh).

According to some aspects, a surgical prosthetic may include a handle coupled to one or more, and in some instances all, of the couplers. In such embodiments, a surgeon may pull the handle to retract the couplers relative to the patch body and/or the second fasteners to shorten a length of the couplers extending between the patch body and the second fasteners, thereby applying tension to the patch body. Without wishing to be bound by theory, such a configuration may allow a surgeon to simultaneously apply even tension to all of the couplers and/or to a subset of adjacent coupler to achieve a desired tension in the patch body. In some applications, the handle may be used for gross adjustment of the tension applied to the patch body, and individual couplers can be manually adjusted (e.g., by individually retracting the couplers to achieve a desired tension) to perform fine adjustment of the tension applied to the patch body as desired. After the patch body has been sufficiently tensioned, the couplers may be secured in place, such as via a one-way suture and/or ratcheting configuration as discussed above, or by tying off each coupler. Subsequently, the couplers may be cut and the handle may be removed. Depending on the particular embodiment, the couplers may be secured to the handle in any suitable manner, such as via corresponding engaging structures, tying the couplers to the handle, adhesives, clamping arrangements, the couplers may be integrally formed with the handle, and/or any other appropriate construction. Moreover, it should be understood that the current disclosure is not limited to prosthetics including a handle to retract the couplers relative to the patch body and/or second fasteners. For example, each coupler may be tensioned and secured individually to achieve a desired patch body tension in some embodiments.

In some embodiments, a plurality of fasteners (i.e., first fasteners or second fasteners) may be coupled to one another via a support. For example, in one embodiment, a plurality of first fasteners may comprise a plurality of barbed tacks (or other suitable fasteners) spaced along a first support (e.g., a semi-rigid bar, a rail, a strip, etc.) that extends along the first portion of the patch body. Similarly, a plurality of second fasteners may be coupled to one another via a second support that is configured to be indirectly coupled to a second portion of the patch body via a plurality of couplers extending from the second support and/or second fasteners. In certain embodiments, each of the second fasteners may have a corresponding coupler substantially aligned with second fasteners along the second support. In some embodiments, the couplers may be attached to the second support via one or more connectors located on the second support that are constructed and arranged to receive the couplers. Alternatively or additionally, some or all of the couplers extending from the second support may not be aligned with the second fasteners, and/or a number of couplers extending between the second portion of the patch body may be different than a number of second fasteners coupled to the second support (i.e., more couplers than fasteners, or fewer couplers than fasteners).

According to some aspects, surgical prosthetics including fasteners provided on one or more supports to attach portions of a patch body to tissue (directly and/or indirectly) may provide for easier fixation of the fasteners to tissue, for example, by maintaining an alignment and/or spacing of the fasteners when they are fastened to the tissue. Moreover, in some instances, such configurations may aid in applying a uniform tension to the patch body, for example, by aiding in distributing forces applied to the patch body when retracting the couplers relative to the patch body and/or second fasteners to shorten a length of the couplers extending between the patch body and the second fasteners.

It should be understood that the current disclosure is not limited to any particular arrangement for the first and/or second supports. For example, a support may be attached to any suitable number and/or type of fasteners, and the fasteners may be arranged according to any suitable spatial distribution and/or arrangement along the support. In some embodiments, the fasteners may be integrally formed with the support to form a unitary structure. Alternatively, a support may include features to facilitate attachment of the fasteners to the support. Moreover, it should be understood that different arrangements of fasteners may be utilized for different portions of a patch body (e.g., first and second portions), and/or a support may be employed only along one portion of the patch body.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 is a perspective view of one embodiment of a prosthetic 100 for augmenting or repairing a tissue defect such as a ventral or incisional hernia. The prosthetic includes a patch body 102 (e.g., a surgical mesh) and a first plurality of fasteners 108 attached to a first portion 104 of the patch body 102. A second plurality of fasteners 110 are attached to a second portion 106 of the patch body via a plurality of couplers 112 extending between the second portion 106 of the patch body and each of the second fasteners 110. In this manner, the second fasteners 110 are indirectly attached to the patch body via the couplers. As discussed above, the fasteners 108 and 110 may have any suitable structure, such as barbed tacks, surgical staples, sutures, adhesives, and/or any other structure suitable for attachment to tissue. In the depicted embodiment, the first portion 104 and second portion 106 of the patch body 102 are along opposing edges of the patch body, though it should be understood that in other embodiments, the fasteners 108 and/or 110 may be attached to other portions of the patch body, such as portions inset from the edges, as the current disclosure is not limited in this regard.

In the depicted embodiment, the first fasteners 108 are attached to a first support 116 extending along the first portion 106 of the patch body 102. Similarly, the second fasteners 110 are attached to a second support 118. As discussed above, the fasteners may be attached to the supports in any suitable manner, and in some instances, may be integrally formed with the supports. Moreover, it should be understood that the supports may be made from any suitable material, such as the same material as the fasteners, patch body, and/or another suitable material that is compatible with the tissue the repair prosthetic is attached to. In some instances, the material and/or configuration of the support(s) may be selected to provide a desired mechanical rigidity. For example, in some applications it may be beneficial for the supports to be semi-rigid to provide structural support to facilitate placement and fixation of the fasteners while also being flexible enough, for example, to allow a surgeon to manipulate portions of the support and fasteners independently while fixating the fasteners. Additionally, as noted above, in some instances, the supports may aid in distributing forces applied to the patch body, which may aid in the patch body being tensioned uniformly, if desired.

Each of the couplers 112 extends from the second portion 106 of the patch body 102 to the second fasteners 110 along the second support 118. Moreover, in the depicted embodiment, the couplers extend through grommets 114 formed in, or attached to, the second portion 106 of the patch body. In this manner, the couplers may be retracted relative to the second portion of the patch body by pulling the couplers 112 through the grommets 114. As a result of such retraction of the couplers relative to the patch body, the length of the couplers extending between the second portion of the patch body and the second fasteners is shortened, which results in the second portion of the patch body being drawn towards the second fasteners and tension being applied to the patch body.

While the couplers 114 and second fasteners 112 are depicted as substantially aligned with one another, it should be understood that other arrangements may be suitable. For instance, in other embodiments, the couplers may be attached to the support 118 at locations between the second fasteners 112. Moreover, as noted above, in some embodiments, the number of couplers may be more, or less, than the number of second fasteners. Additionally, while the depicted embodiment includes a plurality of individual couplers attached to the patch body and second support at individual attachment points, other constructions are also contemplated. For example, in some embodiments, a single coupler may be attached to multiple second fasteners and/or multiple locations along the second portion of the body, such as via a looped, zigzag, or other suitable arrangement for the coupler.

In the depicted embodiment, the couplers 112 are connected to a handle 120 that may facilitate simultaneous retraction of all of the attached couplers relative to the patch body. While a single handle attached to all of the couplers is shown in FIG. 1, other arrangements are also contemplated. For instance, other embodiments may include multiple handles connected to subsets of the couplers, which may allow for individual groups of couplers to be retracted to tension different portions of the patch body. Moreover, as described in more detail below, a handle may not be included in some embodiments, and each coupler may be retracted relative to the patch body and/or the second fasteners individually.

Figure 2:
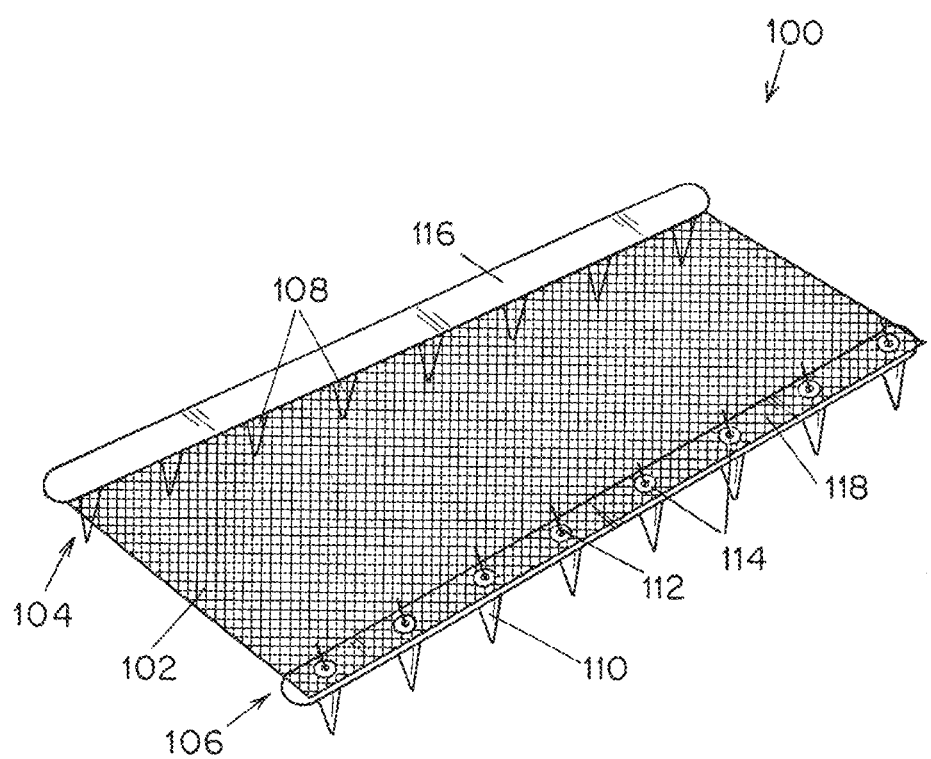
FIG. 2 is schematic perspective view of the surgical prosthetic of FIG. 1 with tension applied to the patch body.

Referring now to FIG. 2, the prosthetic 100 of FIG. 1 is shown in a configuration after tensioning the patch body. As illustrated, shortening the length of the couplers extending between the second portion 106 of the patch body and the second fasteners 110 (e.g., by pulling the handle 120 away from the patch body and/or toward the second fasteners 110), causes the second portion 106 of the patch body to be drawn toward the second fasteners 110, thereby tensioning the patch body. In some instances, depending on the specific construction and how far the couplers 112 are retracted, the second portion 106 of the patch body 102 may at least partially overlie the second fasteners 110 and/or support 118 after tensioning the patch body 102, as illustrated in FIG. 2. Moreover, in the depicted embodiment, the grommets 114 are substantially aligned with the second fasteners 110 after the patch body is tensioned. However, it should be understood that other arrangements may be suitable. For example, in some embodiments, the second portion of the patch body may remain spaced from the second fasteners and/or second support after the patch body is tensioned. In such embodiments, a length of the couplers 112 may extend between the second portion 106 of the patch body 102 and the second fasteners 110 and/or second support 118 when the patch body is tensioned.

As shown in FIG. 2, after tensioning the patch body 102, the couplers 112 may be secured to the second portion 106 of the patch body to maintain a desired length of the couplers extending between the second portion of the patch body and the associated second fasteners 110. As also shown in figure, in some instances, any excess length of the couplers extending through the patch body (e.g., through the grommets 114) may be trimmed. As a result, the handle 120 (shown in FIG. 1) may be removed after positioning and tensioning of the patch body of the repair prosthetic. It should be understood that the couplers 112 may be secured to the second portion of the patch body 106 in any suitable manner, such as by tying off the ends of the couplers prior to trimming, or via engagement of a structure on the coupler with the grommets 114 (e.g., a barb on a one-way suture, and/or a pawl or other component of a ratcheting arrangement).

Figure 3:
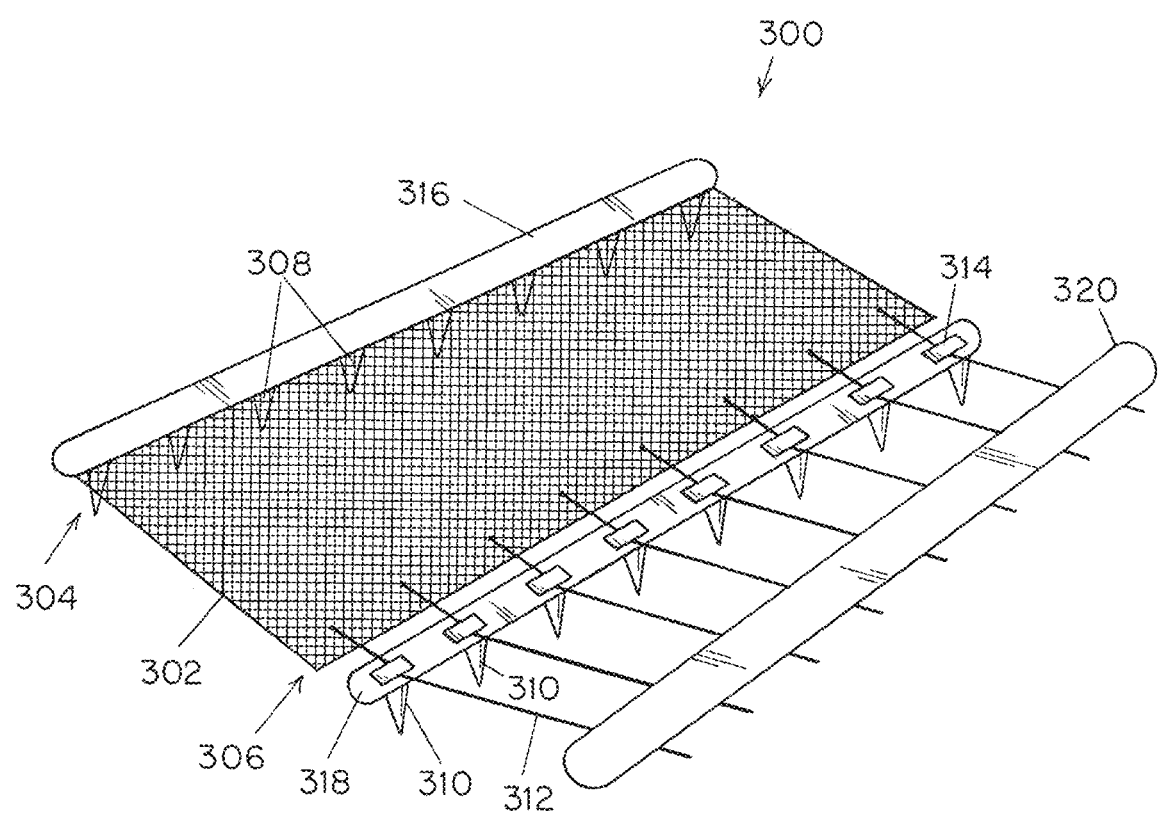
FIG. 3 is a schematic perspective view of a surgical prosthetic, according to another embodiment.

FIG. 3 is a schematic perspective view of another embodiment of a surgical prosthetic 300. Similar to the embodiment discussed above in relation to FIGS. 1 and 2, the prosthetic 300 includes a patch body 302 having a first portion 304 and a second portion 306. A plurality of first fasteners 308 is attached to the first portion 304, and a plurality of second fasteners 310 is attached to the second portion 306 via couplers 312 extending between the second fasteners 310 and the second portion 306 of the patch body. The first fasteners are attached to a first support 316 extending along the first portion 304 of the patch body, and the second fasteners 310 are attached to a second support 318 adjacent the second portion 306 of the patch body.

As illustrated in FIG. 3, the couplers 312 are attached to the second portion 306 and extend through connectors 314 located on the second support 318. For example, the connectors may have an opening or a channel constructed and arranged to slidably receive the couplers such that the couplers 312 may be slidably displaced in at least one direction relative to the second fasteners 310 and/or second support 318 to shorten the length of the couplers and apply tension to the patch body. In this manner, the couplers may be retractable relative to the second fasteners and/or second support via a sliding displacement of the couplers through the connectors. Similar to the embodiment discussed above in connection with FIGS. 1-2, the couplers 312 may be attached to a handle 320 to facilitate simultaneous retraction of multiple couplers, and once a desired tension is achieved in the patch body 302, the couplers may be secured to the second fasteners and/or connectors 314 to secure the patch body in place at the desired tension, and subsequently the couplers may be trimmed and the handle may be removed.

As discussed above, in some embodiments, the couplers of the surgical prosthetics described herein may include features to limit movement of the couplers along one direction relative to the patch body and/or second fasteners. For example, in the embodiment shown in FIGS. 1-2, features on the couplers 112 (such as barbs of a one-way suture and/or components of a ratcheting arrangement) may interact with the grommets 114 to limit the couplers to only be retractable relative to the patch body 102. In this manner, the couplers 114 may be substantially prevented from moving backwards through the grommets upon retracting the couplers relative to the second portion of the patch body to shorten the length of the couplers extending between the second portion 106 of the patch body 102 and the second fasteners. Similarly, in the embodiment shown in FIG. 3, the connectors 314 may include one or more features that interact with corresponding features on the couplers 312 to substantially limit movement of the couplers back through the connectors 314 upon retracting the couplers 312 relative to the second fasteners 310. For example, the connectors may include a structure constructed and arranged to abut barbs on a one-way suture, and/or one or more components of a ratcheting arrangement, such as a pawl or camming surface arranged to engage with associated surfaces on a coupler. Moreover, it should be understood that the current disclosure is not limited to embodiments in which movement of the coupler is limited to one direction relative to the patch body or second fasteners.

Figure 4:
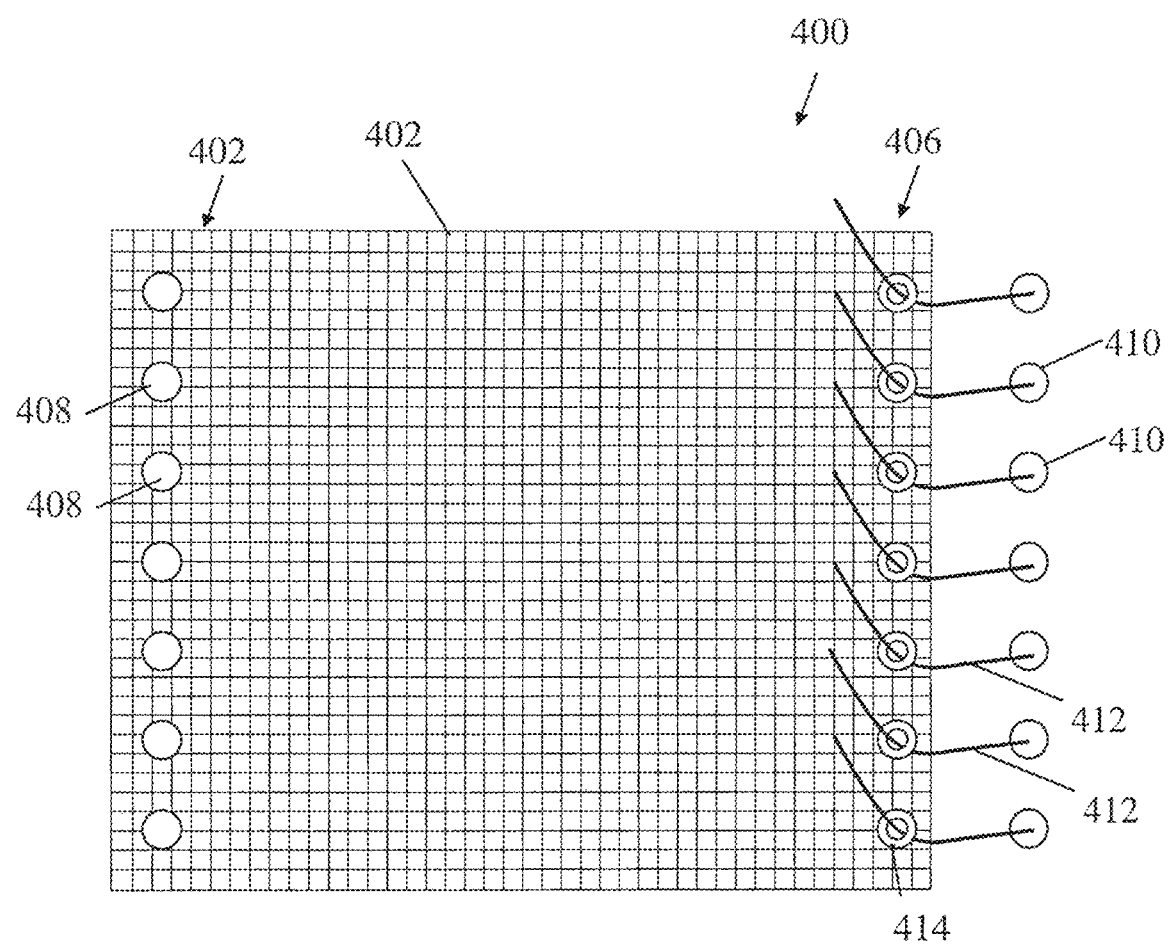
FIG. 4 is a schematic top view of a surgical prosthetic, according to one embodiment.

FIG. 4 is a schematic top view of another embodiment of a prosthetic 400 for augmenting or repairing tissue defects. Similar to the embodiments discussed above, the prosthetic includes a patch body 402 having a first portion 404 and a second portion 406. A plurality of individual first fasteners 408 are attached to the first portion 402 of the patch body, and a plurality of individual second fasteners 410 are attached to the second portion 406 via couplers attached to the second fasteners 410. Specifically, the couplers extend through corresponding grommets 414 attached to the second portion 406. To tension the patch body 402, each coupler may be retracted relative to the second portion 406 to shorten a length of the coupler extending between the second portion 406 and the associated second fastener 410. Once a desired tension is achieved in the patch body 402, each coupler may be secured to the second portion 406 of the patch body to maintain the desired tension.

Figure 5:
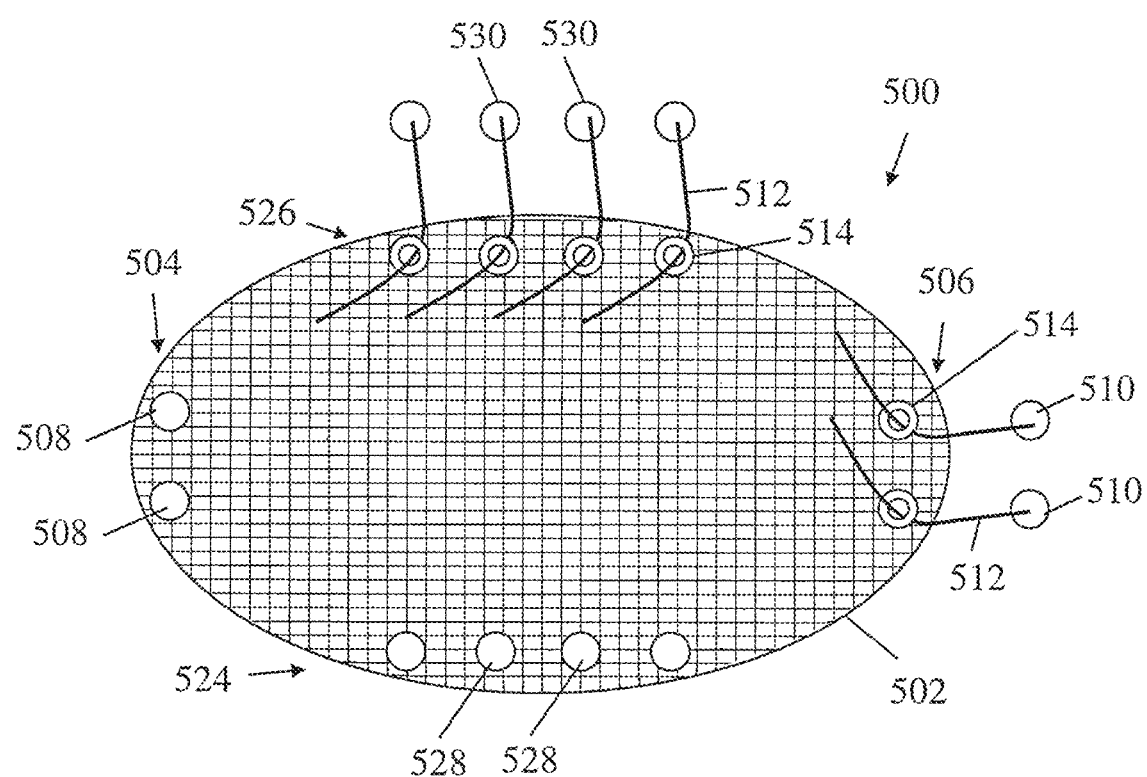
FIG. 5 is a schematic top view of a surgical prosthetic including an oval-shaped patch body, according to one embodiment.

FIG. 5 is a schematic top view of yet another embodiment of a prosthetic 500. In this embodiment, the patch body has an oval shape having a first portion 504, a second portion 506, a third portion 524, and a fourth portion 526. The first portion and second portions 504 and 506 are disposed on opposing sides of the minor axis of the oval, while the third and fourth portions 524 and 526 are on opposing sides of the major axis of the oval. A first plurality of fasteners 508 are attached to the first portion 504 and a second plurality of fasteners 510 are attached to the second portion 506 via couplers 512 extending between the second portion 506 and the second plurality of fasteners 510. Similarly, a third plurality of fasteners 528 is attached to the third portion 524 of the patch body 502, and a fourth plurality of fasteners 530 is attached to the fourth portion 526 of the patch body via couplers 512 extending between the fourth portion 526 and the fourth plurality of fasteners 530. In this embodiment, the patch body may be tensioned independently along two different directions (i.e., along the major and minor axes of the oval-shaped, or other appropriately shaped, patch body 502) by retracting the couplers 512 relative to the second and fourth portions 506, 526 of the patch body (e.g., by pulling the couplers through grommets 514 located in the second and fourth portions.

While rectangular and oval-shaped patch bodies are depicted in the figures, it should be understood that patch bodies having other shapes also may be suitable, and that the current disclosure is not limited to any particular shape for the patch body.

Figure 6:
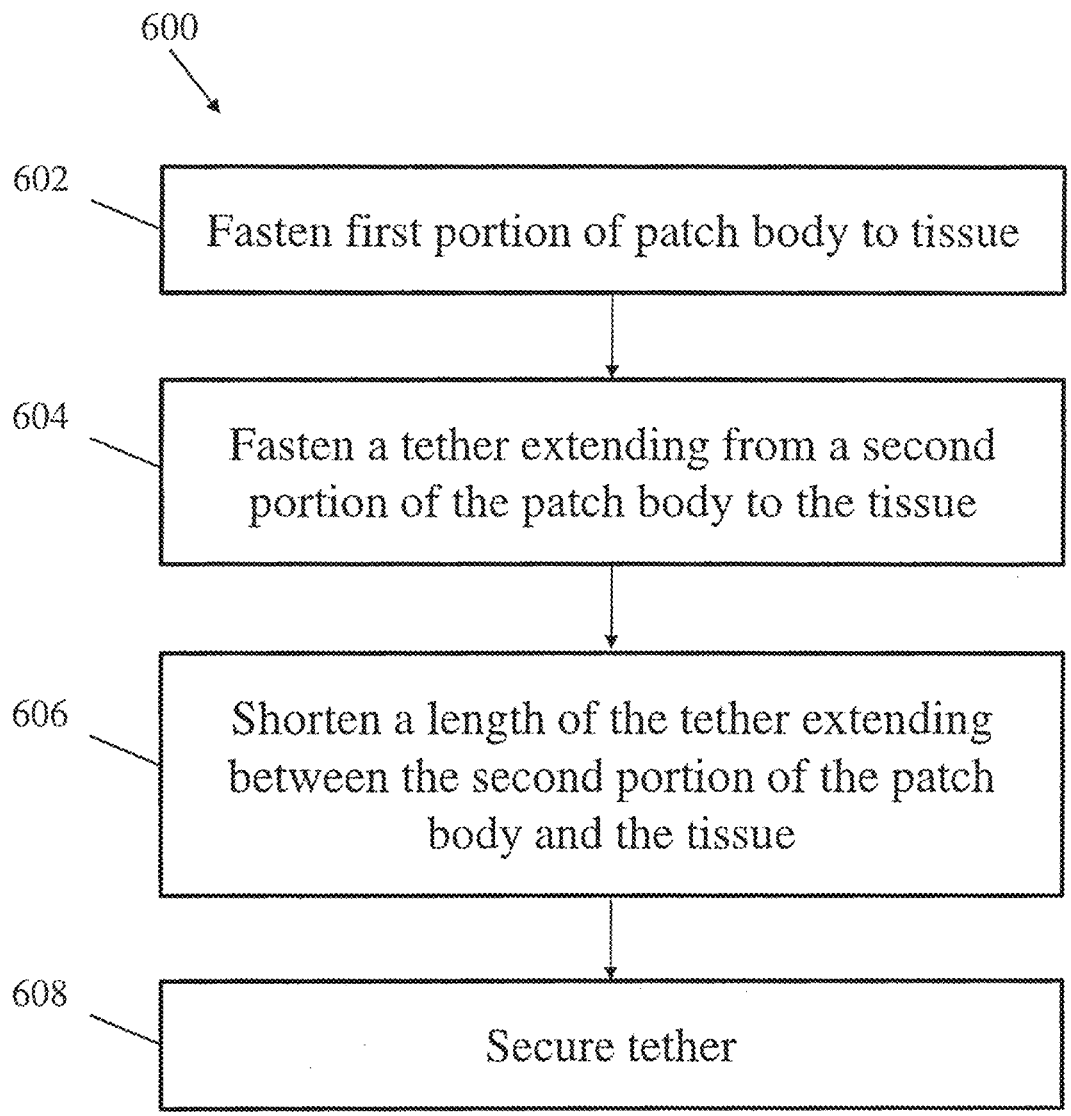
FIG. 6 is a flow chart depicting a method for fixating a prosthetic to tissue, according to one embodiment.

Having described various embodiments of surgical prosthetics, a method 600 for fixating a prosthetic to tissue is described in more detail in connection with FIG. 6. As shown at step 602, the method includes fastening a first portion of a patch body of the repair prosthetic to tissue (e.g., via one or more first fasteners). At step 604, a coupler extending from a second portion of the patch body is fastened to tissue (e.g., via a second fasteners attached to the coupler). At step 606, a length of the coupler extending between the second portion of the patch body and the tissue is shortened to tension the patch body. As described above, such shortening of the length of the coupler may be achieved by retracting the coupler relative to the second portion of the patch body or relative to a second fastener to which the coupler is attached. In some embodiments, shortening the length of the coupler extending between the second portion of the patch body and the tissue may include pulling a handle to which the coupler is attached, though embodiments in which the couplers are shortened by pulling on the individual couplers are also envisioned as the disclosure is not so limited. Moreover, as noted above, in some applications, a handle may be used to perform gross adjustment of the tension applied to a patch body, and individual couplers may be manually adjusted to perform fine adjustments of the patch body tension. Once a desired tension is achieved in the patch body, the coupler is secured at step 608. For example, the coupler may be secured to the second portion of the patch body or to a second fastener. However, embodiments in which the one or more couplers are automatically secured at a desired length using an appropriate construction to provide one way movement of a coupler are also contemplated Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Moreover, the present teachings encompass various alternatives, modifications, and equivalents, as will be appreciated by those of skill in the art. Accordingly, the foregoing description and drawings are by way of example only.

Also, the embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

What is claimed is:

1. A prosthetic for augmenting or repairing a tissue defect, the prosthetic comprising:
   a patch body;
   a first fastener attached to a first portion of the patch body;
   a plurality of couplers attached to and extending from a second portion of the patch body;
   a plurality of second fasteners, wherein each fastener of the plurality of second fasteners is attached to the second portion of the patch body via the plurality of couplers; and
   a handle, wherein
   at least one of the first fastener and the plurality of second fasteners is configured to be attached to tissue, wherein the handle is attached to each coupler of the plurality of couplers, and wherein each coupler of the plurality of couplers is retractable relative to the patch body to shorten a length of the plurality of couplers extending between the second portion of the patch body and the plurality of second fasteners.

2. The prosthetic of claim 1, wherein the length of each coupler of the plurality of couplers extending between the second portion of the patch body and the plurality of second fasteners is constructed and arranged to be shortened to apply tension to the patch body.

3. The prosthetic of claim 2, wherein each coupler of the plurality of couplers comprise at least one selected from the group of a one-way suture and a ratcheting arrangement.

4. The prosthetic of claim 1, wherein the first portion of the patch body is located along a first edge of the patch body, and the second portion of the patch body is located along a second edge of the patch body opposite the first edge.

5. The prosthetic of claim 1, wherein the first fastener is one of a plurality of first fasteners, and each fastener of the plurality of first fasteners is attached to the first portion of the patch body.

6. The prosthetic of claim 5, further comprising a first support attached to and configured to extend along the first portion of the patch body, wherein each fastener of the plurality of first fasteners is attached to the first support.

7. The prosthetic of claim 6, wherein each fastener of the plurality of first fasteners is integrally formed with the first support.

8. The prosthetic of claim 6, further comprising a second support, wherein each fastener of the plurality of second fasteners is attached to the second support.

9. The prosthetic of claim 8, wherein each fastener of the plurality of second fasteners is integrally formed with the second support.

10. The prosthetic of claim 1, further comprising a plurality of grommets located in the second portion of the patch body, wherein each coupler of the plurality of couplers passes through a respective grommet.

11. The prosthetic of claim 1, wherein the first fastener and each fastener of the plurality of second fasteners comprise at least one selected from the group of a tack, a staple, a suture, and an adhesive.

12. A prosthetic for augmenting or repairing a tissue defect, the prosthetic comprising:
    a patch body;
    a first support attached to a first portion of the patch body;
    a first plurality of fasteners attached to the first support;
    a plurality of couplers attached to and extending from a second portion of the patch body;
    a second support attached to the second portion of the patch body via the plurality of couplers; and
    a second plurality of fasteners attached to the second support,
    wherein at least one of the first plurality of fasteners and the second plurality of fasteners is configured to be attached to tissue, wherein each coupler of the plurality of couplers is a flexible structure, and wherein each coupler of the plurality of couplers is retractable relative to the patch body to shorten a length of each coupler of the plurality of couplers extending between the second portion of the patch body and the second plurality of fasteners.

13. The prosthetic of claim 12, wherein the length of each coupler of the plurality of couplers extending between the second portion of the patch body and the second support is constructed and arranged to be shortened to apply tension to the patch body.

14. The prosthetic of claim 13, wherein each coupler of the plurality of couplers comprises at least one selected from the group of a one-way suture and a ratcheting arrangement.

15. The prosthetic of claim 12, wherein the first portion of the patch body is located along a first edge of the patch body, and the second portion of the patch body is located along a second edge of the patch body opposite the first edge.

16. The prosthetic of claim 12, wherein each of the first and second supports is semi rigid.

17. The prosthetic of claim 12, wherein the first plurality of fasteners is integrally formed with the first support, and the second plurality of fasteners is integrally formed with the second support.

18. The prosthetic of claim 12, further comprising a handle, wherein the handle is attached to each coupler of the plurality of couplers.

19. The prosthetic of claim 12, further comprising a plurality of grommets located in the second portion of the patch body, wherein each coupler of the plurality of couplers passes through a respective grommet.

20. The prosthetic of claim 12, wherein the fasteners of the first and second pluralities of fasteners comprise at least one selected from the group of tacks, staples, sutures, and adhesives.

* * * * *